US00PP14907P2

(12) United States Plant Patent
Heims

(10) Patent No.: US PP14,907 P2
(45) Date of Patent: Jun. 15, 2004

(54) TIARELLA PLANT NAMED 'PIRATE'S PATCH'

(50) Latin Name: *Tiarella hybrid*
Varietal Denomination: Pirate's Patch

(75) Inventor: Daniel M. Heims, Portland, OR (US)

(73) Assignee: Terra Nova Nursuries, Inc., Canby, OR (US)

( * ) Notice: Subject to any disclaimer, the term of this patent is extended or adjusted under 35 U.S.C. 154(b) by 47 days.

(21) Appl. No.: 10/654,347

(22) Filed: Sep. 2, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinct cultivar of Tiarella plant characterized by its compact and creeping habit, distinct leaf form and coloration, and with numerous flowering stems and white flowers.

1 Drawing Sheet

Botanical classification: *Tiarella hybrid* (including *Tiarella cordifolia* and *Tiarella wherryi*).
Variety denomination: 'Pirate's Patch'.

BACKGROUND OF THE INVENTION

The present invention relates to a new and distinct cultivar of a hardy herbaceous perennial of the genus Tiarella, and known by the cultivar name 'Pirate's Patch'. The genus Tiarella is a member of the family Saxifragaceae.

The new cultivar originated as a cross between unknown parents. This new Tiarella was one of many seedlings grown from select interspecific hybrids and species that were mass pollinated in the greenhouse in Canby, Oreg. From observation of the characteristics exhibited by the instant plant, it is most likely an interspecific hybrid, including *Tiarella cordifolia,* and *Tiarella wherryi.* As such no species designations are given.

SUMMARY OF THE INVENTION

This plant is characterized by the following:

1. Compact, slow creeping habit.
2. Numerous flowering stems.
3. Attractive maple shaped leaf with strong, dark pattern along main veins.
4. Light pink flower buds and white flower color.
5. Excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
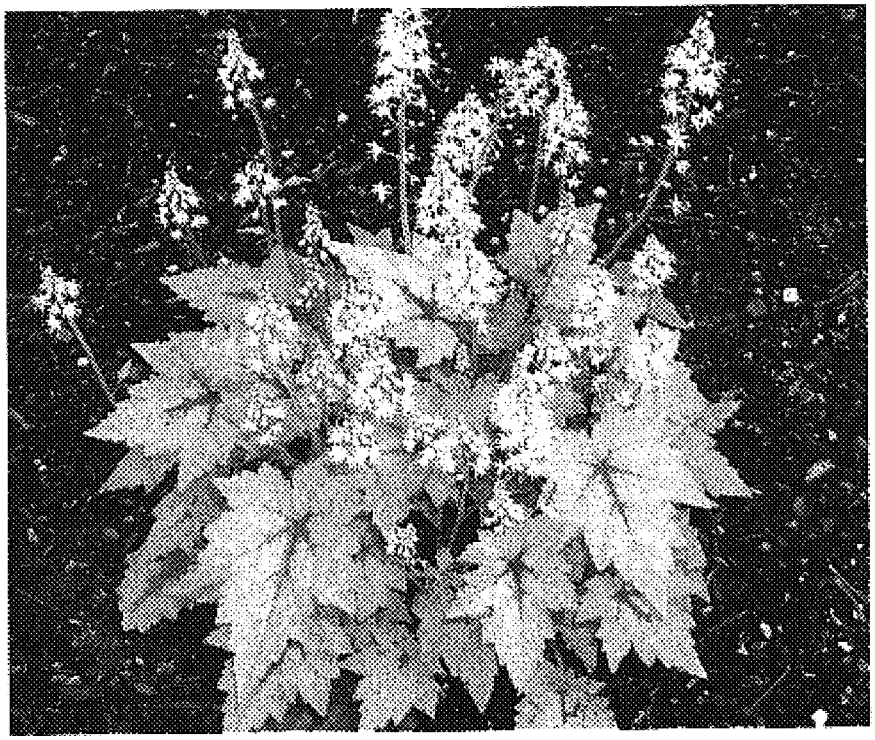
FIG. 1 shows a one year old plant, in flower, growing the in the ground in April in Canby, Oreg.
Figure 2:
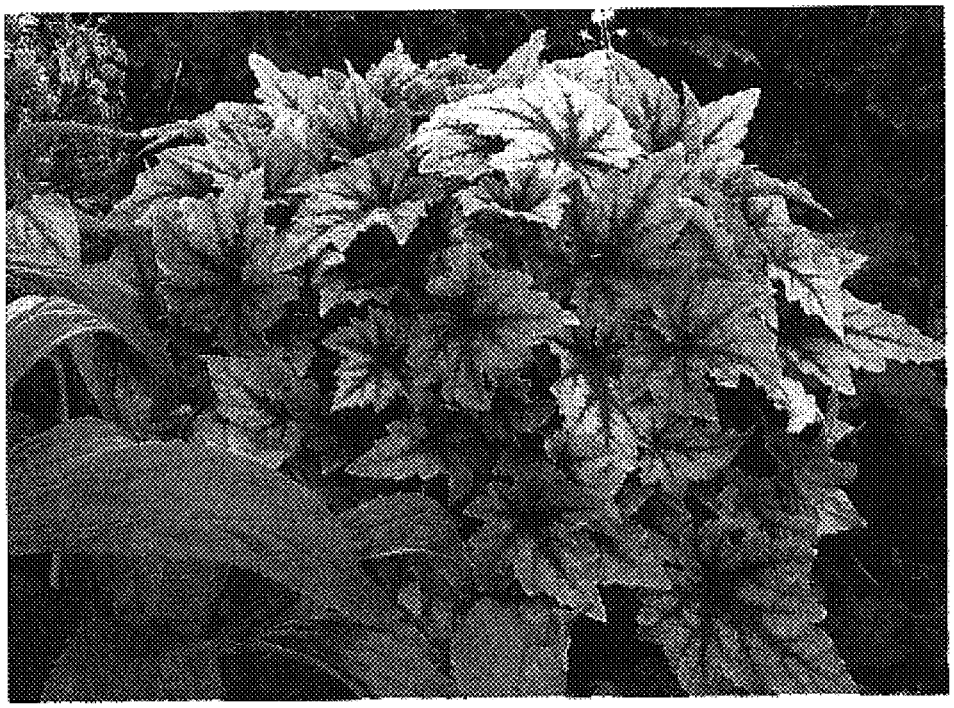
FIG. 2 shows a two-year old plant in a 1 gallon pot in the garden in June in Canby, Oreg.

The following is a detailed description of the new *Tiarella hybrid* based on observations of two-year-old plants grown in the garden in shade in Canby, Oreg. The color descriptions are all based on The Royal Horticultural Society Colour Chart.

Botanical classification: Tiarella hybrid (including *Tiarella cordifolia* and *Tiarella wherryi*).
Variety denomination: 'Pirate's Patch'.
Plant:
- *Type.*—Herbaceous perennial.
- *Hardiness.*—USDA Zones 4 to 9.
- *Form.*—Rhizomatous, herbaceous perennial.
- *Size.*—47 cm wide and 18 cm. high.

Foliage:
- *Type.*—Simple.
- *Arrangement.*—Alternate, when visible on old stems.
- *Shape.*—Ovate.
- *Lobing.*—5 lobed with terminal lobe the longest.
- *Margins.*—Crenate.
- *Venation.*—Palmate.
- *Apex.*—Acute.
- *Base.*—Cordate.
- *Blade length.*—Variable, 7 to 11 cm.
- *Blade width.*—Variable, 6 to 9 cm.
- *Texture.*—Thin, rough.
- *Aspect.*—Matte.
- *Surface.*—Hirsute top and bottom.
- *Petiole length.*—16 cm.
- *Petiole vestiture.*—Hirsute.
- *Petiole color.*—Greyed Orange 177A to Greyed Purple 183D.
- *Leaf color.*—Abaxial—Deep green, Green 137A, with a broad starry pattern of brown maroon, between Brown 200A and Greyed Purple 187A. Late summer older leaves fade to Yellow Green 146. Young spring leaves are Yellow Green 143C with a narrower red starry pattern, Greyed Purple 184A. Adaxial—Green 138C in summer and 143D in spring.

Inflorescence:

*Type.*—Raceme.

*Flower number.*—60 per raceme.

*Bloom period.*—April to May with sporadic rebloom throughout the summer and fall.

*Peduncle.*—Height.—28 cm. Width.—3 mm. at the widest point. Color—Greyed Orange 177A to Greyed Purple 183D. Texture—Glandular-pubescent.

*Pedicel.*—Length—0.8 cm. Texture—glandular. Color—Greyed Purple 183D.

*Lastingness.*—A raceme blooms for about 3 weeks.

Flower bud:

*Size.*—0.4 cm deep and 0.3 cm wide.

*Description.*—Ovoid, downfacing until open.

*Color.*—Pink, Greyed Purple 186C.

Flower:

*Type.*—Perfect, actinomorphic, sepals petaloid.

*Shape.*—Rotate.

*Flower size.*—1 cm wide and 7 mm deep including stamens and pistil.

*Petal number.*—5.

*Petal shape.*—Lanceolate with a clawed base.

*Petal size.*—4 to 5 mm long and 0.6 mm. wide.

*Petal color.*—White 155A.

*Calyx.*—Petaloid, parted almost to the base, reflexed.

*Calyx size.*—0.7 cm. wide and 2 mm. deep.

*Calyx color.*—White 155A.

*Sepal.*—5 in number, lanceolate, lobes 3 mm long and 1.5 mm wide.

*Stamens.*—10, conspicuously exerted.

*Filaments.*—White 155A, 0.6 cm long.

*Anthers undehisced.*—Orange 29A.

*Pollen color.*—Orange 28B.

*Pistil.*—White 155A, 6 mm long.

*Fragrance.*—Sweet.

Fruit:

*Type.*—A one-celled capsule, beak-like, composed of two unequal parts.

*Size.*—0.7 cm long.

*Color.*—Brown 200C.

Seeds:

*Color.*—Black 202A.

*Shape.*—Minute, oval, 1 mm long.

*Fertility.*—Fertile.

Disease resistance: This new hybrid shows good mildew tolerance, the main problem for Tiarella.

COMPARISONS WITH SIMILAR TIARELLA

Compared with Tiarella 'Jeepers Creepers' (U.S. Plant patent application No. 13,437), Tiarella 'Pirate's Patch' has shallower leaf lobes and is not shiny, but matte on the leaf surface. The plant is more compact, with much better flower number and shorter flower stalks. Both are slow creepers.

Compared to Tiarella 'Inkblot', an unpatented plant, the new cultivar is creeping rather then clumping and the pattern in the leaf is much more pronounced.

I claim:

1. A new and distinct cultivar of Tiarella plant characterized by its compact and creeping habit, distinct leaf form and coloration, and with numerous flowering stems and white flowers.

* * * * *